(12) United States Patent
Chen et al.

(10) Patent No.: US 8,471,055 B2
(45) Date of Patent: Jun. 25, 2013

(54) PHOTO-CROSSLINKABLE LIQUID CRYSTAL MONOMERS WITH OPTICAL ACTIVITY

(75) Inventors: Yu-hsien Chen, Kaohsiung (TW); Sheng-fa Liu, Zhudong Township (TW); Huai-an Li, Zhongli (TW); Sin-min Fuh, Zhongli (TW); Hong-cheu Lin, Hsinchu (TW); Huang-ming Chen, Zhubei (TW); Po-jen Yang, Wuqi Township (TW); Shin-chieh Chien, Tucheng (TW)

(73) Assignees: Chunghwa Picture Tubes, Ltd., Bade, Taoyuan (TW); National Chiao Tung University, Hsinchu (TW)

( * ) Notice: Subject to any disclaimer, the term of this patent is extended or adjusted under 35 U.S.C. 154(b) by 85 days.

(21) Appl. No.: 13/209,414

(22) Filed: Aug. 14, 2011

(65) Prior Publication Data

US 2012/0289731 A1     Nov. 15, 2012

(30) Foreign Application Priority Data

May 10, 2011   (TW) .............................. 100116314 A

(51) Int. Cl.
C07C 69/76      (2006.01)

(52) U.S. Cl.
USPC .......................................................... 560/59

(58) Field of Classification Search
USPC .......................................................... 560/59
See application file for complete search history.

(56) References Cited

U.S. PATENT DOCUMENTS

| | | | |
|---|---|---|---|
| 5,886,242 A | 3/1999 | Etzbach et al. | |
| 6,025,899 A | 2/2000 | Fukunaga et al. | |
| 6,678,024 B2 | 1/2004 | Kim | |
| 7,098,974 B2 | 8/2006 | Ko | |
| 7,294,303 B2 | 11/2007 | Fukuoka et al. | |
| 2006/0077325 A1 | 4/2006 | Li et al. | |
| 2006/0209238 A1 | 9/2006 | Shiraogawa et al. | |
| 2007/0090326 A1 | 4/2007 | Bai et al. | |
| 2007/0228325 A1 | 10/2007 | Yumoto | |

OTHER PUBLICATIONS

Hsu etal, Synthesis and Characterization of Ferroelectric Liquid Crystalline Polysiloxanes and Polymethacrylates Containing [(S)-2-Methyl-1-butoxy]phenyl 4-(alkyloxy)biphenyl-4'-carboxylate Side Groups, Macromolecules 1992, 25, p. 7126-7134.*

(Continued)

*Primary Examiner* — Taylor Victor Oh
(74) *Attorney, Agent, or Firm* — Cheng-Ju Chiang

(57) ABSTRACT

The present invention relates to photo-crosslinkable liquid crystal monomers with optical activity. The liquid crystal monomers contains one chiral center with an acrylate group or terminal diacrylate groups, and terminal dibenzene rings are introduced in order to extend its hard segment for the purpose of getting a wider liquid crystalline phase. By introducing the liquid crystal monomers, the room temperature nematic liquid crystal or the cholesteric liquid crystal may have a better mutual solubility and a wider, steadier structure of liquid crystal. The liquid crystal monomers have the following formula structure:

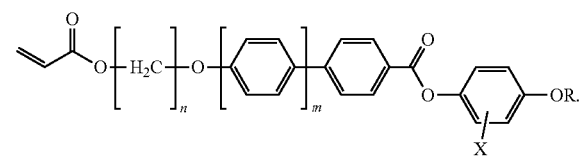

7 Claims, 1 Drawing Sheet

OTHER PUBLICATIONS

Johan Lub; Wim P. M. Nijssen; Rene T. Wegh; Joost P. A. Vogels; Ana Ferrer, "Synthesis and Properties of Photoisomerizable Derivatives of Isosorbide and Their Use in Cholesteric Filters," Advanced Functional Material, 2005, pp. 1961-1972, vol. 15, Wiley-VCH Verlag G mb H & Co. KGaA, Weinheim, Germany.

H. Guillard; P. Sixou; L. Reboul; A. Perichaud, "Electrooptical Characterizations of Polymer Stabilized Cholesteric Liquid Crystals", Polymer, 2001, pp. 9753-9762, vol. 42, Elsevier Science LTD.

Timothy J. White, Rebecca L. Bricker; Lalgudi V. Natarajan; Svetlana V. Serak; Nelson V. Tabiryan; Timothy J. Bunning, "Polymer Stabilization of Phototunable Cholesteric Liquid Crystals", Soft Matter, Jul. 23, 2009, pp. 3623-3628, vol. 5, The Royal Society of Chemistry.

A. C. Tasolamprou; M. Mitov; D. C. Zografopoulos; E. E. Kriezis, "Theoretical and Experimental Studies of Hyperreflective Polymer-Network Choiesteric Liquid Crystal Structures with Helicity Inversion", Optics Communications, 2009, pp. 903-907, vol. 282, Elsevier B. V.

Johan Lub; Peter Van De Witte; Ciska Doornkamp, Joost P. A. Vogels; Rene T. Wegh, "Stable Photopatterned Cholesterin Layers Made by Photoisomerization and Subsequent Photopolymerization for Use as Color Filters in Liquid-Crystal Displays", Advanced Materials, Sep. 3, 2003, pp. 1420-1425, vol. 15, No. 17, Wiley-VCH Verlag GmbH & Co., K GaA, Weinheim, Germany.

\* cited by examiner

PHOTO-CROSSLINKABLE LIQUID CRYSTAL MONOMERS WITH OPTICAL ACTIVITY

FIELD OF THE INVENTION

The present invention relates to liquid crystal monomers, especially relates to a photo-crosslinkable liquid crystal monomers containing a chiral center with an acrylate group or terminal diacrylate groups.

BACKGROUND OF THE INVENTION

Cholesteric liquid crystal (CLC) reflective technology is a technology which utilizes several bistable liquid crystal monomers having similar molecular structures to cholesterol, to reflect colorful light according to the molecular torsion state. Macromolecular Liquid Crystalline Films (MLCF), which can be created from adding a polymer containing an acrylate group to the CLC structure further curing by UV, have special optical properties to be applicable to various display devices. The CLC molecule has a spiral structure which can selectively reflect wavelength of the MLCF. The bands of the reflected wavelength are related to the pitches of the CLC molecule, which can be represented by the following equation (1).

$$\lambda = np \quad (1),$$

wherein $\lambda$ is a reflective wavelength, p is a pitch of the CLC molecule, and n is a value of the dielectric anisotropy of the cholesteric phase.

Pitches of the CLC molecule can be changed in different ways to control bands of the reflection of the MLCF to create red, green, or blue light. Conventionally known photo-crosslinkable compound having a chiral center can be added into room temperature nematic liquid crystal (NLC) or CLC to get a wider reflection band and a higher reflective intensity of the liquid crystal by controlling the concentrations thereof. When the concentrations are increased, the pitches of the CLC molecule are also increased. Then, a polymer is added into the CLC, and after photocrosslinking reaction, the polymer will have chain reactions to wrap up the CLC molecules, making the CLC change from a liquid state to a solid state. Thus, adding a photo-crosslinkable compound can control the color and color saturation of the reflection of the room temperature NLC or CLC.

Please refer to FIG. 1. FIG. 1 is a diagram illustrating a relationship between wavelength and reflectance of the reflection of CLC molecules. The CLC molecules form a macromolecule membrane after polyreaction. The wavelength of the reflection of the CLC molecules can be adjusted by adding various concentrations of the chiral molecules. The CLC molecules which are added different amounts of chiral molecules have different helical twisting power (HTP) to vary due to added amounts, thus reflection wavelength can be fallen blue, green, or red band.

Currently known optically active compounds have low HTP, which cause poor compatibility between the optically active compounds and the CLC, and do not have a liquid crystalline phase. In addition, in order to get the desired reflecting property of the CLC, there needs to be added more optically active compounds.

Thus, there is a need for an improved optically active compound to overcome the above-mentioned difficulties.

SUMMARY OF THE INVENTION

The purpose of the present invention is to provide a photo-crosslinkable liquid crystal monomers having optical activity thereby with chemical structures to strengthen the HTP and to have a liquid crystalline phase. By introducing the present invention, the room temperature nematic liquid crystal (NLC) or the cholesteric liquid crystal (CLC) may have a better mutual solubility, as well as a wider and steadier structure of liquid crystal.

Therefore, the present invention provides photo-crosslinkable liquid crystal monomers with optical activity, wherein a formula thereof is:

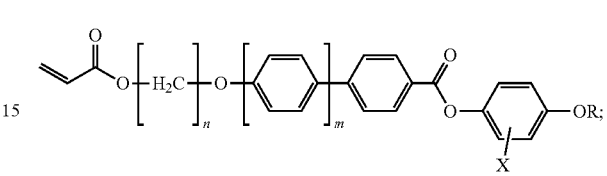

wherein n is an integer from 4 to 8;
m is an integer from 1 to 3;
X is hydrogen, halogens, cyano or thiocyano, or nitro, and X is at a para position, an ortho position, or a meta position of the alkoxy groups; and
R is C1-10 alkyl.

The C1-10 alkyl is a straight-chain or a branched alkyl group which comprises 1-10 carbon atoms, such as: methyl, ethyl, n-propyl, isopropyl, n-butyl, isobutyl, tert-butyl, sec-butyl, n-amyl, isopentyl, neopentyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 3,3-dimethylbutyl, n-heptyl, 1-methylhexyl, 2-methylhexyl, 3-methylhexyl, 4-methylhexyl, 5-methylhexyl, 1,1-dimethylpentyl, n-octyltin, 1-methylheptyl, 2-methylhepty, 3-methylhepty, 4-methylhepty, n-nonyl, 1-methyloctyl, 2-methyloctyl, 3,6-dimethylheptyl, decyl, 1-methylnonyl, etc.

In a preferred embodiment of the present invention, R is C6-10 alkyl. That is, said C6-10 alkyl is a straight-chain or a branched alkyl group which comprises 6-10 carbon atoms. It is especially preferable, where R is (s)-1-methylheptyl or (s)-3,6-dimethylheptyl.

The halogen is fluorine, chlorine, bromine, or iodine.

In a preferred embodiment of the present invention, n is 6.
In a preferred embodiment of the present invention, m is 1.
In a preferred embodiment of the present invention, X is hydrogen or halogens, and more preferably X is hydrogen.
In a preferred embodiment of the present invention, R is C6-10 alkyl. It is especially preferable where R is (s)-1-methylheptyl or (s)-3,6-dimethylheptyl.

In a further preferred embodiment of the present invention, n is 6, m is 1, X is hydrogen or halogens, and R is C6-10 alkyl.

Compared with the prior art, the positive effects of the present invention are as follows.

1) By introducing a chiral center, the present invention increases the HTP value to control the pitches of the CLC molecule. By introducing an end position-acrylate group, the CLC molecules can form a macromolecule membrane after polyreaction, and by adjusting the concentrations of the added chiral molecules, a CLC membrane can be made to reflect particular light and can be used in reflective liquid-crystal E-book.

2) The liquid crystal monomers of the present invention contains liquid crystalline phase. When they are introduced into the room temperature nematic liquid crystal (NLC) or the cholesteric liquid crystal (CLC), they will have a higher compatibility with the liquid crystal, and better mutual solubility as well as a wider and steadier structure of liquid crystal.

DESCRIPTION OF THE INVENTION

Figure 1:
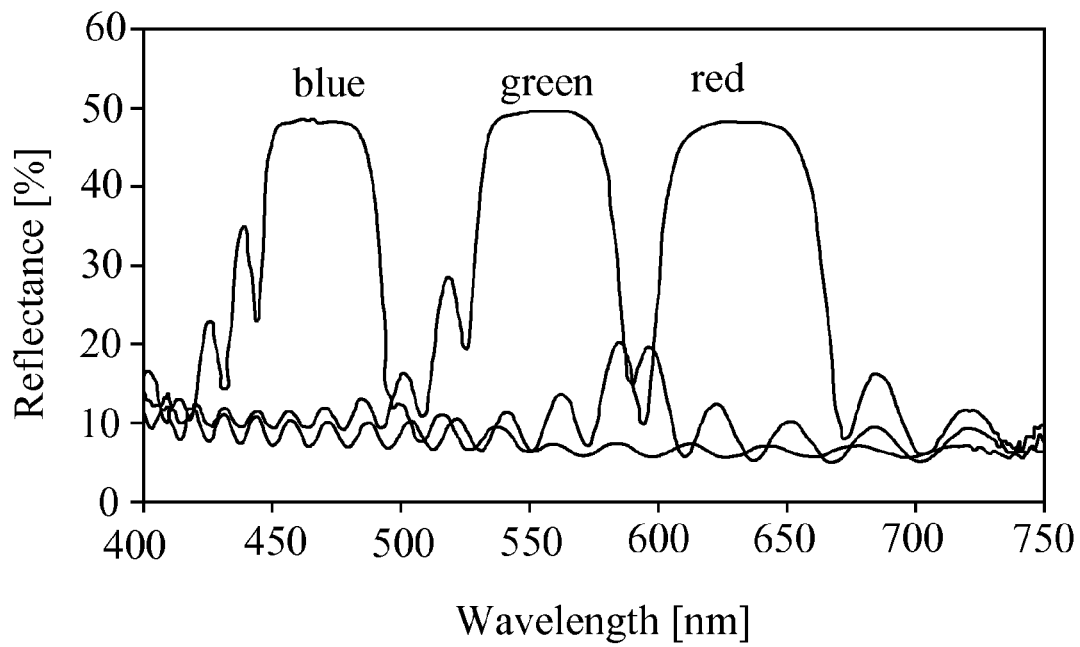
FIG. 1 is a diagram illustrating relationship between wavelength and reflectance of the reflection.
Figure 2:
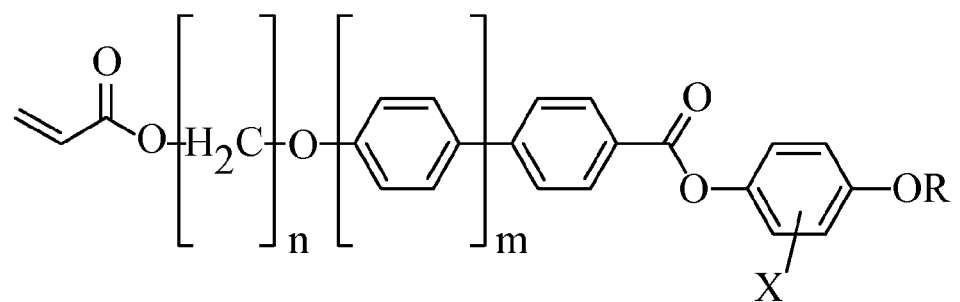
FIG. 2 is a formula of photo-crosslinkable liquid crystal monomers of the present invention with optical activity.

The present invention provides photo-crosslinkable liquid crystal monomers with optical activity, wherein a formula thereof which is shown in FIG. 2 is:

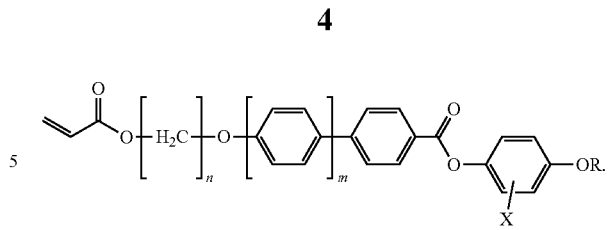

Example 1 n is 6, m is 1, X is hydrogen, R is (s)-1-methylheptyl. Thus the formula is:

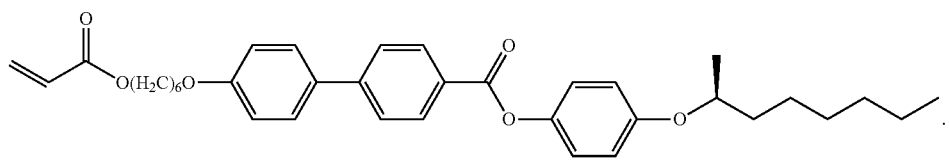

The scheme is as follows.

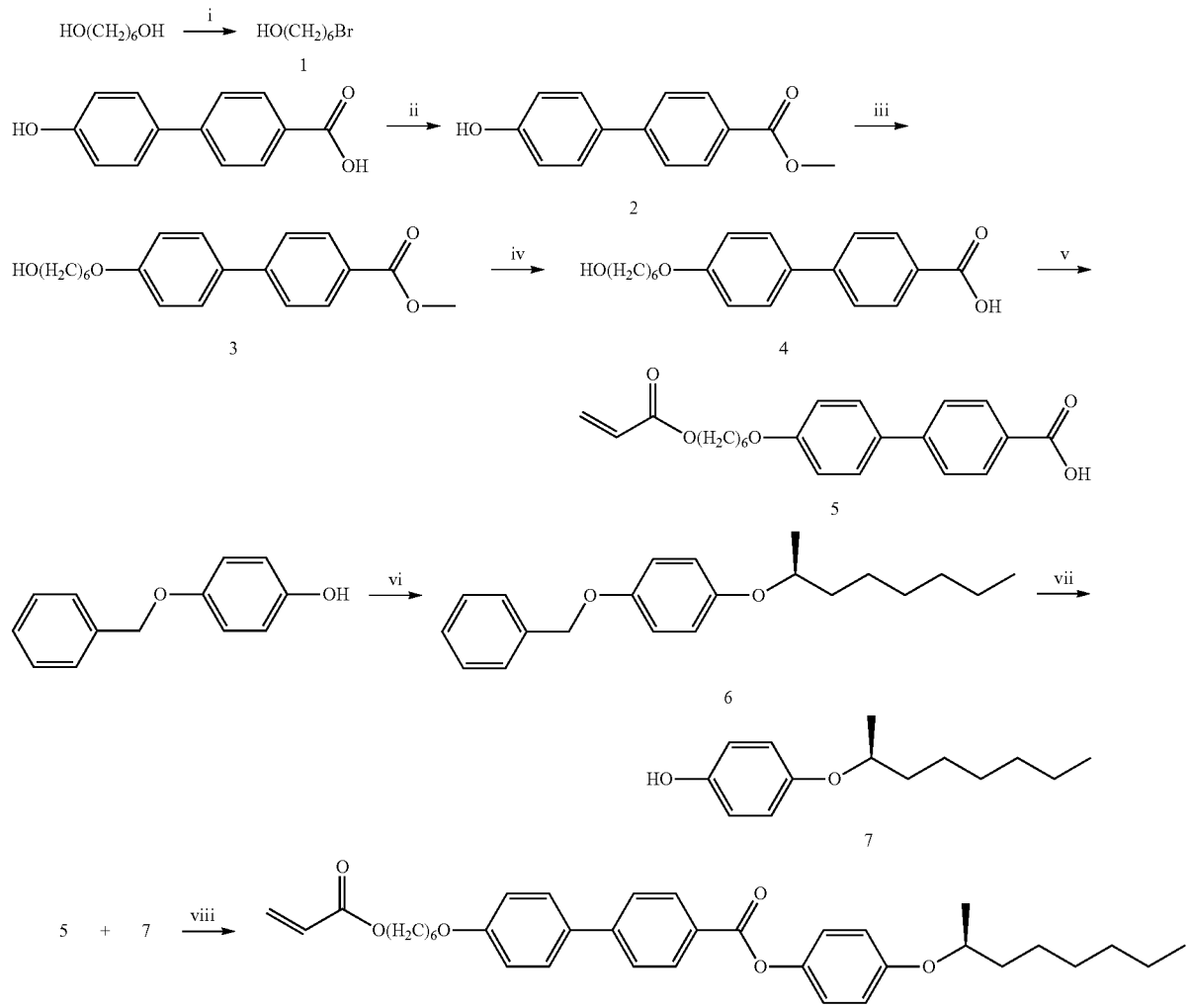

The preparation method thereof is as follows:

i) Preparing 6-bromo-1-hexanol.

Putting 1,6-hexanediol (20 g) and 48% (wt %) HBr into a reacting bottle (500 mL), adding toluene (200 mL) followed by stirring and refluxing at 80° C. for 24 hours. Then cooling to the room temperature, removing the solvent by a rotary vacuum evaporator, drying with anhydrous magnesium sulfate to gain crude product, wherein column chromatography of the crude product is carried out to gain pure 6-bromo-1-hexanol (22.85 g). The yield is about 75%.

ii) Preparing

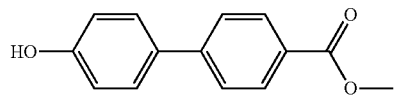

methyl 4'-hydroxy[1,1'-biphenyl]-4-carboxylate.

Dissolving 4'-hydroxy-4-biphenylcarboxylic acid (5 g) in methanol (50 mL), adding sulfuric acid (98% wt., 2 mL) and toluene (10 mL) followed by heating and refluxing for 12 hours. Then cooling to room temperature, extracting with water and ethyl acetate, drying with anhydrous magnesium sulfate to gain crude product, wherein column chromatography of the crude product is carried out to gain a pure target compound (5.22 g). The yield is about 98%.

iii) Preparing

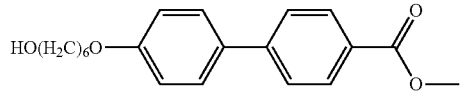

methyl 4'-(6-hydroxyhexyloxy)-[1,1'-biphenyl]-4-carboxylate.

Putting the product of step (ii) (5 g), 6-bromo-1-hexanol (4 g) and potassium iodide into a reacting bottle (500 mL), adding acetone followed by stirring. Then adding potassium carbonate solution (20 mL) followed by heating and refluxing for 24 hours. Then cooling to room temperature, removing the solvent by a rotary vacuum evaporator, column chromatography of the crude product is carried out to gain a pure target compound (6.61 g). The yield is about 95%.

iv) Preparing

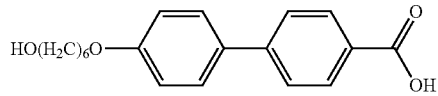

4'-(6-hydroxyhexyloxy)-[1,1'-biphenyl]-4-carboxylic acid.

Dissolving the product of step (iii) (5 g) into a reacting bottle (500 mL), adding ethanol (180 mL) followed by stirring. Adding potassium hydroxide solution (20 mL) followed by heating and refluxing for 12 hours. Then cooling to the room temperature followed by removing the solvent by a rotary vacuum evaporator. Dissolving the product in water followed by adding hydrochloric acid slowly, and then the solids start to be separated out till the pH value is 3. Then allow it to stand for half an hour, and then get the solids after filtration. The solids are dried by a vacuum drying chamber and recrystallized by ethanol, to gain a pure target compound (4.65 g). The yield is about 97%.

v) Preparing

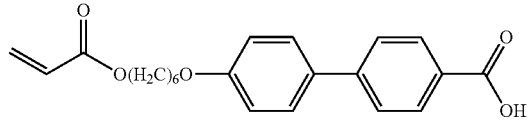

4'-(6-acryloxy-hexyl-1-oxy)-[1,1'-biphenyl]-4-carboxylic acid.

Putting the product of step (iv) (2 g) and 2,6-di-tert-butyl-4-methylphenol into a two-neck bottle (250 mL), and then vacuuming for 1 hour. Under the protection of nitrogen, adding 1,4-dioxane as a solvent followed by adding 2,6-di-tert-butyl-4-methylphenol under room temperature. After 30 minutes, acrylyl chloride (0.6 mL) was dropped slowly into the bottle on ice bath. Heating to 50° C. and refluxing for 5 hours. Cooling to the room temperature, cold dilute hydrochloric acid (50%, wt.) was dropped slowly into the bottle, and then the solids start to be separated out. Extracting by water and dichloromethane, drying with anhydrous magnesium sulfate, removing the solvent by a rotary vacuum evaporator, column chromatography of the crude product is carried out to gain a pure target compound (1.69 g). The yield is about 72%.

vi) Preparing

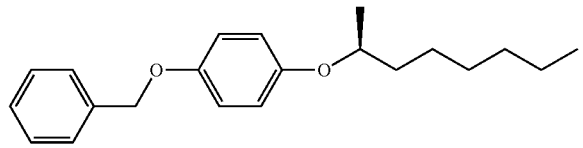 [SMILES: CCCCCC[C@H](C)Oc1ccc(OCc2ccccc2)cc1]

(s)-1-benzyloxy-4-[(1-methylheptyl)oxy]benzene.

Putting 4-benzyloxyphenol (5 g) and triphenyl phosphine (23.58 g) into a two-neck bottle (500 mL), and then vacuuming for 1 hour. Under the protection of nitrogen, adding dichloromethane (150 mL) followed by stirring to dissolve. Adding diethyl azodicarboxylate (22.73 g) into the bottle on ice bath followed by stirring. Adding (s)-2-octylchloride (13.36 g), reacting 24 hours under room temperature. Extracting by water and dichloromethane, drying with anhydrous magnesium sulfate, removing the solvent by a rotary vacuum evaporator, column chromatography of the crude product is carried out to gain a pure target compound (19.41 g). The yield is about 83%.

vii) Preparing

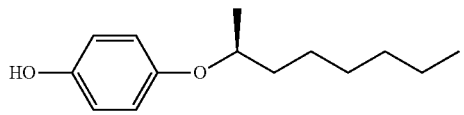 [SMILES: CCCCCC[C@H](C)Oc1ccc(O)cc1]

(s)-4-[(1-methylheptyl)oxy]phenol.

Adding the product of step (vi) (5 g) and 10% Pd/C into a reacting bottle (500 mL), and then vacuuming for 1 hour. Under the protection of nitrogen, adding tetrahydrofuran (150 mL), adding hydrogen followed to react 10 hours, filtering the Pd/C after the reaction. Removing the solvent by a rotary vacuum evaporator, column chromatography of the crude product is carried out to gain a pure target compound (3.38 g). The yield is about 95%.

viii) Preparing the final target compound, which is:

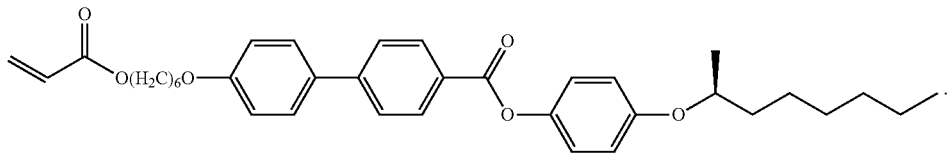

(s)-4-[(1-methylheptyl)oxy]phenol-4'-(6-acryloxy-hexyl-1-oxy)-[1,1'-biphenyl]-4-carboxylate.

Putting the product of step (vii) (1.01 g), the product of step (v) (2 g) and 4-dimethylamiopryidine (0.03 g) into a reacting bottle (500 mL), and then vacuuming for 1 hour. Under the protection of nitrogen, adding dichloromethane as a solvent, react 30 minutes. Then adding dicyclohexylcarbodiimide (DCC, 1.41 g), react 12 hours under the room temperature. Extracting by water and dichloromethane, drying with anhydrous magnesium sulfate, column chromatography of the crude product is carried out to gain a pure target compound (1.81 g). The yield is about 70%.

Example 2

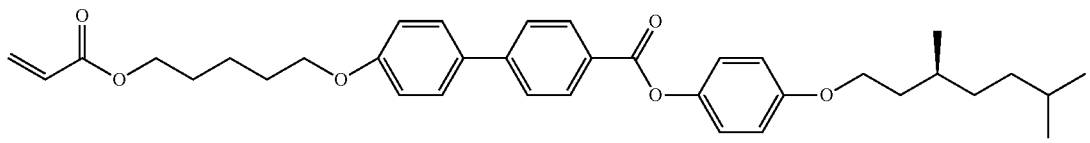

The preparation method thereof is as follows:

i) Preparing 6-bromo-1-hexanol.

Putting 1,6-hexanediol (20 g) and 48% (wt %) HBr into a reacting bottle (500 mL), adding toluene (200 mL) followed by stirring and refluxing at 80° C. for 24 hours. Then cooling to the room temperature, removing the solvent by a rotary vacuum evaporator, drying with anhydrous magnesium sulfate to gain crude product, wherein column chromatography of the crude product is carried out to gain pure 6-bromo-1-hexanol (22.85 g). The yield is about 75%.

ii) Preparing

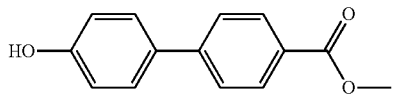

methyl 4'-hydroxy[1,1'-biphenyl]-4-carboxylate.

Dissolving 4'-hydroxy-4-biphenylcarboxylic acid (5 g) in methanol (50 mL), adding sulfuric acid (98% wt., 2 mL) and toluene (10 mL) followed by heating and refluxing for 12 hours. Then cooling to the room temperature, extracting with water and ethyl acetate, drying with anhydrous magnesium sulfate to gain crude product, wherein column chromatography of the crude product is carried out to gain a pure target compound (5.22 g). The yield is about 98%.

iii) Preparing

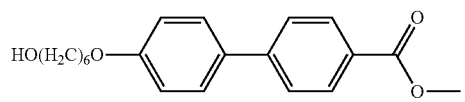

methyl 4'-(6-hydroxyhexyloxy)-[1,1'-biphenyl]-4-carboxylate.

Putting the product of step (ii) (5 g), 6-bromo-1-hexanol (4 g) and potassium iodide into a reacting bottle (500 mL), adding acetone (180 mL) followed by stirring. Then adding potassium carbonate solution (20 mL) followed by heating and refluxing for 24 hours. Then cooling to the room temperature, removing the solvent by a rotary vacuum evaporator, column chromatography of the crude product is carried out to gain a pure target compound (6.61 g). The yield is about 95%.

iv) Preparing

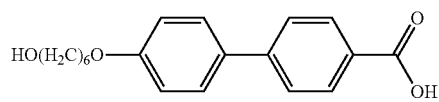

4'-(6-hydroxyhexyloxy)-[1,1'-biphenyl]-4-carboxylic acid.

Dissolving the product of step (iii) (5 g) into a reacting bottle (500 mL), adding ethanol (180 mL) followed by stirring. Adding potassium hydroxide solution (20 mL) followed by heating and refluxing for 12 hours. Then cooling to the room temperature followed by removing the solvent by a rotary vacuum evaporator. Dissolving the product in water followed by adding hydrochloric acid slowly, and then the solids start to be separated out till the pH value is 3. Then stand it for 10 minutes, and then get the solids after filtration. The solids are dried by a vacuum drying chamber and recrystallized by ethanol, and then we gain a pure target compound (4.65 g). The yield is about 97%.

v) Preparing

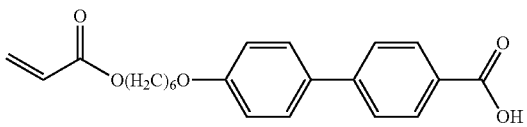

4'-(6-acryloxy-hexyl-1-oxy)-[1,1'-biphenyl]-4-carboxylic acid.

Putting the product of step (iv) (2 g) and 2,6-di-tert-butyl-4-methylphenol into a two-neck bottle (250 mL), and then vacuuming for 1 hour. Under the protection of nitrogen, adding 1,4-dioxane as a solvent followed by adding 2,6-di-tert-butyl-4-methylphenol under the room temperature. After about half an hour, acrylyl chloride (0.6 mL) was dropped slowly into the bottle on ice bath. Heating to 50° C. and refluxing for 5 hours. Cooling to the room temperature, cold dilute hydrochloric Acid (50%, wt.) was dropped slowly into the bottle, and then the solids start to be separated out. Extracting by water and Dichloromethane, drying with anhydrous magnesium sulfate, removing the solvent by a rotary vacuum evaporator, column chromatography of the crude product is carried out to gain a pure target compound (1.69 g). The yield is about 72%.

vi) Preparing (s)-1-benzyloxy-4-[(3,6-dimethylheptyl)oxy]benzene.

Putting 4-benzyloxyphenol (5 g) and triphenyl phosphine (23.58 g) into a two-neck bottle (250 mL), and then vacuuming for 1 hour. Under the protection of nitrogen, adding dichloromethane (150 mL) followed by stirring to dissolving. Adding diethyl azodicarboxylate (22.73 g) into the bottle on ice bath followed by stirring. Then adding (s)-3,6-dimethyloctylchloride (15.01 g), reacting 24 hours under the room temperature. Extracting by water and dichloromethane, drying with anhydrous magnesium sulfate, removing the solvent by a rotary vacuum evaporator, column chromatography of the crude product is carried out to gain a pure target compound (20.26 g). The yield is about 83%.

vii) Preparing (s)-4-[(3,6-dimethylheptyl)oxy]phenol.

Adding the product of step (vi) (5 g) and 10% Pd/C into a reacting bottle (500 mL), and then vacuuming for 1 hour. Under the protection of nitrogen, adding tetrahydrofuran (150 mL), adding hydrogen followed to react 10 hours, filtering the Pd/C after the reaction. Removing the solvent by a rotary vacuum evaporator, column chromatography of the crude product is carried out to gain a pure target compound (3.59 g). The yield is about 95%.

viii) Preparing the final target compound, which is

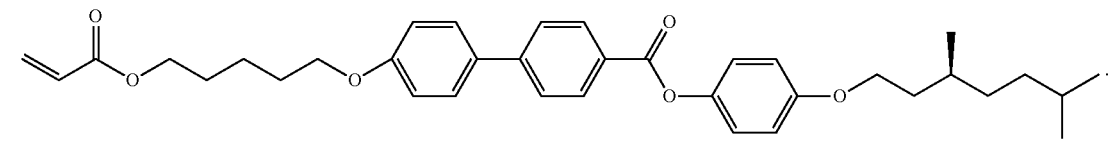 [SMILES: C=CC(=O)OCCCCCOc1ccc(-c2ccc(C(=O)Oc3ccc(OCC[C@@H](C)CCC(C)C)cc3)cc2)cc1 ; "."]

(s)-4-[(3,6-dimethylheptyl)oxy]phenol-4'-(6-acryloxy-hexyl-1-oxy)-[1,1'-biphenyl]-4-carboxylate.

Putting the product of step (vii) (1.07 g), the product of step (v) (2 g) and 4-dimethylamiopryidine (0.03 g) into a reacting bottle (500 mL), and then vacuuming for 1 hour. Under the protection of nitrogen, adding dichloromethane as a solvent, react 30 minutes. Then adding dicyclohexylcarbodiimide (DCC, 1.41 g), react 12 hours under the room temperature. Extracting by water and dichloromethane, drying with anhydrous magnesium sulfate, column chromatography of the crude product is carried out to gain a pure target compound (1.85 g). The yield is about 70%.

Example 3

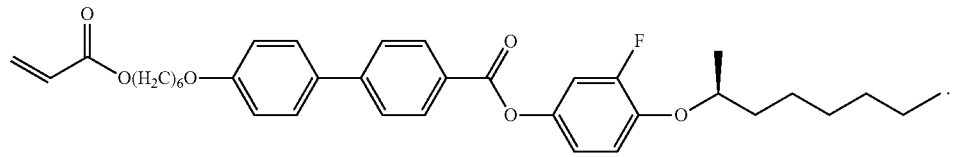

The preparation method thereof is as follows:

i) Preparing 6-bromo-1-hexanol.

Putting 1,6-hexanediol (20 g) and 48% (wt %) HBr into a reacting bottle (500 mL), adding Toluene (200 mL) followed by stirring and refluxing at 80° C. for 24 hours. Then cooling to the room temperature, removing the solvent by a rotary vacuum evaporator, drying with anhydrous magnesium sulfate to gain crude product, wherein column chromatography of the crude product is carried out to gain pure 6-bromo-1-hexanol (22.85 g). The yield is about 75%.

ii) Preparing

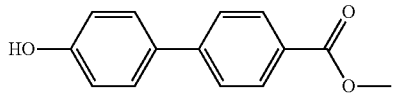 [SMILES: COC(=O)c1ccc(-c2ccc(O)cc2)cc1]

methyl 4'-hydroxy[1,1'-biphenyl]-4-carboxylate.

Dissolving 4'-hydroxy-4-biphenylcarboxylic acid (5 g) in methanol (50 mL), adding sulfuric acid (98% wt., 2 mL) and Toluene (10 mL) followed by heating and refluxing for 12 hours. Then cooling to the room temperature, extracting with water and ethyl acetate, drying with anhydrous magnesium sulfate to gain crude product, wherein column chromatography of the crude product is carried out to gain a pure target compound (5.22 g). The yield is about 98%.

iii) Preparing

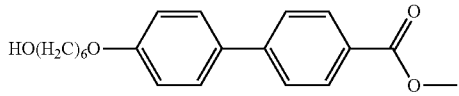

methyl 4'-(6-hydroxyhexyloxy)-[1,1'-biphenyl]-4-carboxylate.

Putting the product of step (ii) (5 g), 6-bromo-1-hexanol (4 g) and potassium iodide into a reacting bottle (500 mL), adding acetone (180 mL) followed by stirring. Then adding potassium carbonate solution (20 mL) followed by heating and refluxing for 24 hours. Then cooling to the room temperature, removing the solvent by a rotary vacuum evaporator, column chromatography of the crude product is carried out to gain a pure target compound (6.61 g). The yield is about 95%.

iv) Preparing

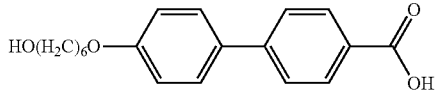

4'-(6-hydroxyhexyloxy)-[1,1'-biphenyl]-4-carboxylic acid.

Dissolving the product of step (iii) (5 g) into a reacting bottle (500 mL), adding ethanol (180 mL) followed by stirring. Adding potassium hydroxide solution (20 mL) followed by heating and refluxing for 12 hours. Then cooling to the room temperature followed by removing the solvent by a rotary vacuum evaporator. Dissolving the product in water followed by adding hydrochloric acid slowly, and then the solids start to be separated out till the pH value is 3. Then stand it for 10 minutes, and then get the solids after filtration. The solids are dried by a vacuum drying chamber and recrystallized by ethanol, and then we gain a pure target compound (4.65 g). The yield is about 97%.

v) Preparing

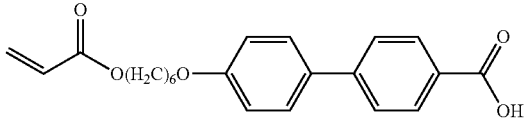

4'-(6-acryloxy-hexyl-1-oxy)-[1,1'-biphenyl]-4-carboxylic acid.

Putting the product of step (iv) (2 g) and 2,6-di-tert-butyl-4-methylphenol into a two-neck bottle (250 mL), and then vacuuming for 1 hour. Under the protection of nitrogen, adding 1,4-dioxane as a solvent followed by adding 2,6-di-tert-butyl-4-methylphenol under the room temperature. After about half an hour, acrylyl chloride (0.6 mL) was dropped slowly into the bottle on ice bath. Heating to 50° C. and refluxing for 5 hours. Cooling to the room temperature, cold dilute hydrochloric acid (50%, wt.) was dropped slowly into the bottle, and then the solids start to be separated out. Extracting by water and dichloromethane, drying with anhydrous magnesium sulfate, removing the solvent by a rotary vacuum evaporator, column chromatography of the crude product is carried out to gain a pure target compound (1.69 g). The yield is about 72%.

vi) Preparing (s)-1-bromo-2-fluoro-4-[(1-methylheptyl)oxy]benzene.

Putting 4-bromo-3-fluorophenol (4.76 g) and phosphorus (23.58 g) into a two-neck bottle (500 mL), and then vacuuming for 1 hour. Under the protection of nitrogen, adding dichloromethane (150 mL) followed by stirring to dissolving. Adding diethyl azodicarboxylate (22.73 g) into the bottle on ice bath followed by stirring. Adding (s)-2-octylchloride (13.36 g), and then reacting 24 hours under the room temperature. Extracting by water and dichloromethane, drying with anhydrous magnesium sulfate, removing the solvent by a rotary vacuum evaporator, column chromatography of the crude product is carried out to gain a pure target compound (18.85 g). The yield is about 83%.

vii) Preparing (s)-2-fluoro-4-[(1-methylheptyl)oxy]phenol-boronic acid.

Adding the product of step (vi) (10 g) into a two-neck bottle. Under the protection of nitrogen, adding tetrahydrofuran (150 mL), cooling to −78° C., adding n-butyllithium (13.90 mL), standing for 2 hours, and then adding triisopropyl borate (14.67 mL). Return to the room temperature, standing for 12 hours, adding hydrochloric acid, extracting by water and dichloromethane, drying with anhydrous magnesium sulfate, removing the solvent by a rotary vacuum evaporator. Recrystallizing by n-hexane, and then we gain a pure target compound (6.65 g). The yield is about 75%.

viii) Preparing (s)-2-fluoro-4-[(1-methylheptyl)oxy]phenol.

Heating and refluxing the product of step (vii) (5 g) and hydrogenperoxide for 24 hours followed by standing for 12 hours. Extracting by water and dichloromethane, drying with anhydrous magnesium sulfate, removing the solvent by a rotary vacuum evaporator, column chromatography of the crude product is carried out to gain a pure target compound (3.05 g). The yield is about 68%.

ix) Preparing the final target compound, which is:

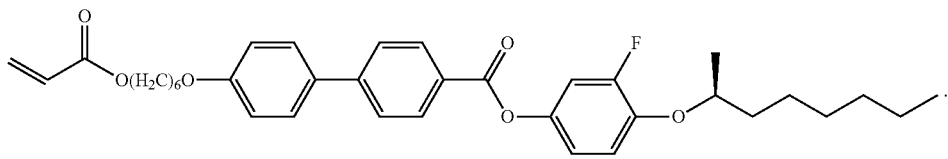

(s)-4-[(1-methylheptyl)oxy]phenol-3-4'-(6-acryloxy-hexyl-1-oxy)-[1,1'-biphenyl]-4-carboxy late.

Putting the product of step (vii) (1.01 g), the product of step (v) (2 g) and 4-dimethylamiopryidine (0.03 g) into a reacting bottle (500 mL), and then vacuuming for 1 hour. Under the protection of nitrogen, adding dichloromethane as a solvent, react 30 minutes. Then adding dicyclohexylcarbodiimide (DCC, 1.41 g), react 12 hours under the room temperature. Extracting by water and dichloromethane, drying with anhydrous magnesium sulfate, column chromatography of the crude product is carried out to gain a pure target compound (1.86 g). The yield is about 70%.

What is claimed is:

1. A photo-crosslinkable liquid crystal monomer with optical activity, having a formula thereof:

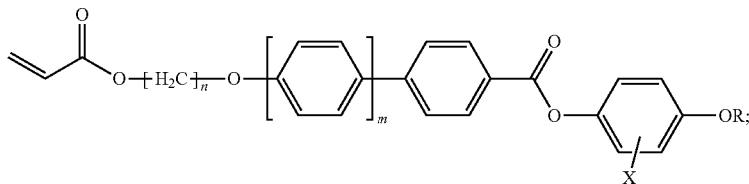

wherein n is an integer from 4 to 8;
m is an integer from 1 to 3;
X is hydrogen, halogen, cyano or thiocyano, or nitro; and
R is (s)-1-methylheptyl, or (s)-3,6-dimethylheptyl.

2. The photo-crosslinkable liquid crystal monomer with optical activity according to claim 1, wherein said n is 6.

3. The photo-crosslinkable liquid crystal monomer with optical activity according to claim 1, wherein said m is 1.

4. The photo-crosslinkable liquid crystal monomer with optical activity according to claim 1, wherein said X is hydrogen or halogens.

5. The photo-crosslinkable liquid crystal monomer with optical activity according to claim 4, wherein said X is hydrogen.

6. The photo-crosslinkable liquid crystal monomer with optical activity according to claim 1, wherein said n is 6, m is 1, X is hydrogen or halogen.

7. The photo-crosslinkable liquid crystal monomer with optical activity according to claim 6, wherein said n is 6, m is 1, X is hydrogen.

* * * * *